US006608884B1

United States Patent
Mazess et al.

(10) Patent No.: US 6,608,884 B1
(45) Date of Patent: Aug. 19, 2003

(54) FLUOROSCOPY MACHINE WITH HEAD MOUNTED DISPLAY

(75) Inventors: Richard B. Mazess, Madison, WI (US); David L. Ergun, Verona, WI (US)

(73) Assignee: Lunar Corporation, Madison, WI (US)

( * ) Notice: Subject to any disclaimer, the term of this patent is extended or adjusted under 35 U.S.C. 154(b) by 40 days.

(21) Appl. No.: 09/619,382

(22) Filed: Jul. 19, 2000

Related U.S. Application Data

(60) Provisional application No. 60/144,673, filed on Jul. 20, 1999.

(51) Int. Cl.[7] ................................................. H05G 1/64
(52) U.S. Cl. ...................... 378/98; 378/98.2; 378/98.8; 378/42; 600/425
(58) Field of Search ................ 378/41, 42, 98.2, 378/98.8, 190, 98, 110, 114; 600/425, 439; 345/786; 257/51

(56) References Cited

U.S. PATENT DOCUMENTS

| | | | | |
|---|---|---|---|---|
| 4,385,397 A | * | 5/1983 | Verro ........................... 378/20 |
| 4,737,972 A | * | 4/1988 | Schoolman ................... 378/41 |
| 5,091,926 A | * | 2/1992 | Horton et al. ............... 378/114 |
| 5,479,185 A | | 12/1995 | Biverot ........................... 345/6 |
| 5,483,961 A | | 1/1996 | Kelly et al. ............... 128/653.1 |
| 5,526,812 A | | 6/1996 | Dumoulin et al. ........ 128/653.1 |
| 5,662,111 A | | 9/1997 | Cosman .................... 128/653.1 |
| 5,729,475 A | | 3/1998 | Romanik, Jr. ................ 364/559 |
| 5,787,886 A | | 8/1998 | Kelly et al. ............... 128/653.1 |
| 5,823,958 A | | 10/1998 | Truppe ......................... 600/426 |

OTHER PUBLICATIONS

"Flock of Birds®," Ascension Technology Corporation, 4 Internet web pages downloaded Jan. 6, 1999.
Virtual Research Systems, Inc., 4 Internet web pages downloaded Jan. 6, 1999 for Head Mount Displays.
The Virtual Reality Source, 5 Internet web pages downloaded Jan. 6, 1999 for ProView 60 and ProView™ Head Mount Displays.
"Insidetrak & Insidetrak HP," The Virtual Reality Source, 3 Internet web pages downloaded Dec. 28, 1998.

* cited by examiner

Primary Examiner—Drew A. Dunn
Assistant Examiner—Therese Barber
(74) Attorney, Agent, or Firm—Quarles & Brady LLP

(57) ABSTRACT

A fluoroscopy machine includes an x-ray source and detector mounted in spaced relation to a support arm, an image processor and a display device. The display device includes image optics attached to a head mount wearable by a person, such as a physician or technician. The image displayed by the image optics can be processed by the image processor to present an orientationally accurate image corresponding to the head mount wearer's field of view. For example, the image can be processed to correct for angle of rotation, translation and/or perspective distortion.

15 Claims, 4 Drawing Sheets

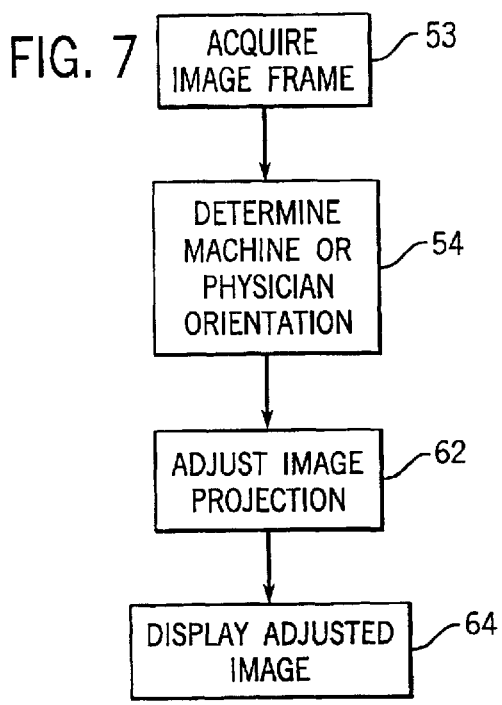
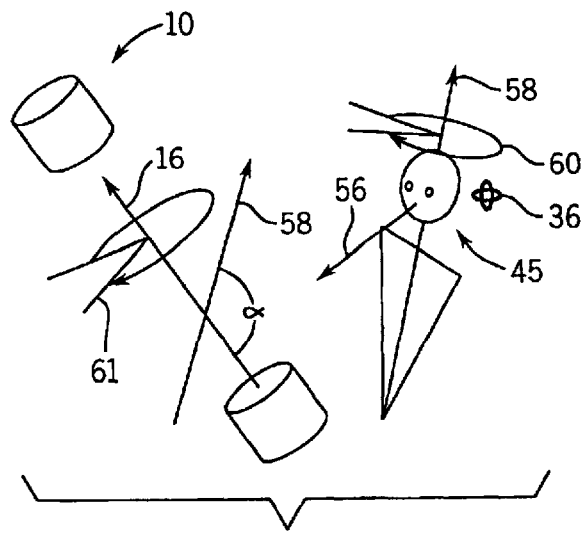
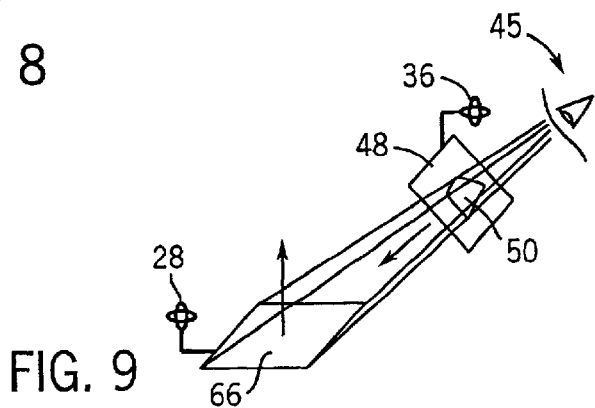

FLUOROSCOPY MACHINE WITH HEAD MOUNTED DISPLAY

CROSS REFERENCE TO RELATED APPLICATIONS

This application hereby claims the benefit of provisional application No. 60/144,673 filed Jul. 20, 1999.

BACKGROUND OF THE INVENTION

This invention relates generally to fluoroscopic x-ray machines, and in particular to a fluoroscopy machine having a head mounted display for providing a real-time x-ray image to a physician.

Early x-ray fluoroscopy machines employed a simple fluorescent screen that could be positioned on one side of a patient opposite an x-ray source. X-rays passing through the patient caused fluorescence of the screen to create an instantaneous or "real-time" x-ray image of the patient. The location of the screen clearly indicated the portion of the patient being imaged and the orientation of the image was, by necessity, always the same as that of the patient.

Although this system was simple and intuitive, a relatively high dose of x-rays was needed to produce an image on the fluorescent screen. For this reason, modern fluoroscopy machines have replaced the simple fluorescent screen, usually, with an image intensifier tube coupled to a video camera. The image intensifier tube employs the mechanism of electron multiplication to greatly increase the flux striking the fluorescent screen, significantly reducing the amount of x-ray exposure required.

The video camera serves to record the image and provides the additional benefit of permitting the x-ray beam to be positioned without regard to the location of the physician who no longer views the fluorescent screen directly, but instead, views a high resolution CRT-type display placed in a convenient location. In order that the display be easily viewed, it may be placed on a stand independent of the rest of the fluoroscopy machine to be positioned in the best viewing location, or supported on adjustable arms to be moved during the course of the fluoroscopic procedure. Nevertheless, the displays are inherently bulky and relatively difficult to reposition, thus hampering the mobility of the physician. For this reason, multiple displays may be placed at different locations around the patient to accommodate physician movement.

By separating the display from the fluorescent screen of the image intensifier, the x-ray image loses its context with the patient. Both the site and orientation of the imaged structure are no longer apparent. For example, the image may often be upside down or in mirror image with respect to the physician's view of the patient and may rotate as the x-ray beam is repositioned as a result of the geometry of the fluoroscopy machine.

While the prior art has addressed the limited problem of image rotation through various means including motors for rotating the video camera with respect to the image intensifier, or by rotating magnetic yokes deflecting the electron beam on the CRT, such systems are imperfect and at best correct only for rotation caused by the movement of the fluoroscopy machine and necessarily fail to account for the movement of the physician which might desirably shift the orientation of the x-ray image.

What is needed is a display system that preserves the complete flexibility of x-ray beam orientation and physician location offered by modern fluoroscopy machines while restoring the intuitive relationship between the x-ray image and the patient found in early fluoroscopy machines.

BRIEF SUMMARY OF THE INVENTION

The present invention employs a head-mounted electronic display, such as has been developed for virtual reality-type systems, to provide a fluoroscopic image in the physician's changing field of view regardless of movement of the physician. The image may be manipulated according to the relative positions of the physician and the fluoroscopy machine to provide an intuitive relationship between the displayed image and the patient either in rotation, translation or apparent perspective.

Specifically, the present invention provides a fluoroscopy machine having an x-ray source producing a beam of x-rays along an axis, and a support arm having a first end attached to the x-ray source and a second end opposite the x-ray source along the axis, the support arm providing a space along the axis between the first and second ends sufficient to accommodate a human patient. An x-ray detector attached to the second end of the arm is positioned to receive the x-rays along the axis and to provide electronic image signals. A head-mounted display provides image optics producing an image from the electronic image signals and viewable by the physician wearing the head mounted display on his or her head.

It is one object of the invention to provide a fluoroscopy machine allowing complete freedom of movement by the physician without the need for multiple display systems or complex gimbaled or articulated display supports. The head-mounted display ensures that the x-ray image is always in the physician's field of view.

The image optics may produce an opaque image blocking the receipt of light through the image from the physician's field of view, or may be transparent to permit the passage of light through the image.

Thus, it is another object of the invention to provide hands free viewing of both the image and other areas of the physician's field of view. When an opaque image is selected it may be displaced from the center of the field of view so as to be visible by eye movement alone.

The fluoroscopy machine may include an input representing an angle of rotation and may further include image processing electronics for rotating the image to the angle of rotation. The input may be the relative angular displacement between the physician's field of view and a reference fixed with respect to the fluoroscopy machine or the patient.

Thus, it is another object of the invention to provide automatic correction of the image rotation to comport with the viewpoint of the physician as the physician moves with respect to either the fluoroscopy machine or the patient.

The fluoroscopy machine may include an input representing a translation, and may include further, an image processor for translating the image within the field of view of the physician based on that input. The input may be the relative displacement between the physician's field of view and a reference fixed with respect to the fluoroscopy machine or the patient.

Thus, it is another object of the invention to allow the image to be electronically "attached" to the patient or the fluoroscopy machine so as to provide an intuitive reference frame between the image and patient or fluoroscopy machine.

The fluoroscopy machine may include an input representing a skewing, and may further include an image processor skewing of the image as a function of the input. The input may be a relative displacement and orientation between the physician's field of view and a predetermined image plane fixed with respect to the image intensifier or the patient.

Thus, it is another object of the invention to impose perspective effects on the image so that the image is not only attached to a reference point in the real world, but appears to conform to a reference plane as well so as to provide an "x-ray vision" type display.

The foregoing and other objects and advantages of the invention will appear from the following description. In this description, reference is made to the accompanying drawings which form a part hereof and in which there is shown by way of illustration the preferred embodiment of the invention. Such embodiment does not necessarily represent the full scope of the invention, however, and reference must be made therefore to the claims for interpreting the scope of the invention.

BRIEF DESCRIPTION OF THE SEVERAL VIEWS OF THE DRAWINGS

FIG. 7 is a flowchart showing the principal steps performed by the image processor of FIG. 2 in producing the image of FIG. 6;

FIG. 8 is a schematic perspective representation of a physician and a fluoroscopy machine showing relevant measurements for rotational correction of the image of FIG. 5; and FIG. 9 is a schematic perspective representation of a perspective correction employed in the generation of the image of FIG. 6.

DETAILED DESCRIPTION OF THE INVENTION

Figure 1:
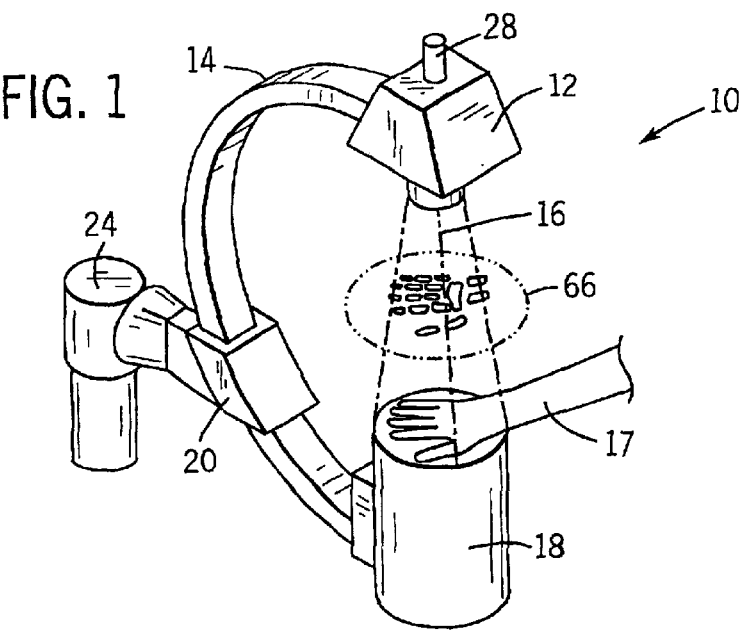
FIG. 1 is a perspective view of a compact fluoroscopy machine as may be viewed by a physician, showing an x-ray source projecting x-rays toward an image intensifier, the latter covered, in part, by a patient's hand and further showing the projection of an x-ray image produced by the fluoroscopy machine in fixed location above the image intensifier as is possible with the present invention.

Referring now to FIG. 1, a fluoroscopy machine 10 includes an x-ray source 12, being an x-ray tube of conventional design, attached at a first end of a C-arm 14 to project x-rays along an axis 16 bisecting the circle of the C-arm 14. A second end of the C-arm 14 supports an image intensifier/camera unit 18 positioned to receive x-rays along the axis 16 while providing a gap between the x-ray source 12 and the image intensifier/camera unit 18 to receive a patient.

The C-arm 14 is supported by a collar 20 to slide therein, which in turn is supported to be easily positioned around several axes by gimble assembly 24. Collar 20 and gimble assembly 24 may instrumented so as to provide electronic signals indicating the orientation and location of the axis 16.

Figure 2:
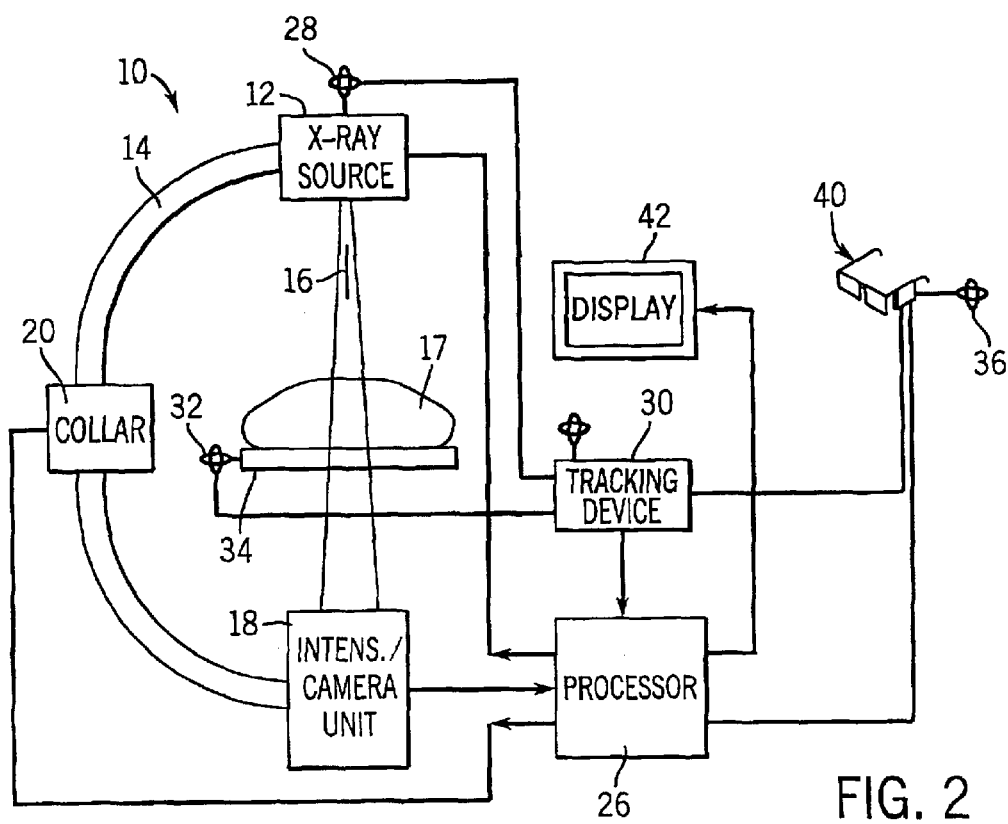
FIG. 2 is a block diagram of a fluoroscopy machine similar to that of FIG. 1 but including a patient support, and further showing three, three-dimensional tracking devices fixed to the x-ray source and used by an image processor, the patient support and a head-mounted display to be worn by the physician.

Referring also to FIG. 2, the electronic signals from the collar and gimble assembly 24 and other mechanical position signals relating to the position of the axis 16 as may be understood in the art, may be provided to an image processor 26 whereby the relative orientation of axis 16 with respect to a stationary reference may be calculated.

Alternatively or in addition, a three-dimensional tracking antenna 28 may be attached to the x-ray source 12 (or any mechanical element fixed with respect to the x-ray source 12) so as to provide identical information about the position of axis 16. In the present example, the three-dimensional tracking antenna 28 is of a type currently used in virtual reality systems and employs a stationary three-dimensional tracking receiver 30 which may detect and quantify movements of the antenna 28. Such tracking systems are commercially available from Polhemus of Colchester, Vt. under the tradename INSIDETRAK and from Ascension Technology Corporation of Burlington, Vt. under the tradename FLOCK OF BIRDS. Such systems desirably provide real-time measurements of six degrees of freedom of antenna 28 in x, y and z of Cartesian coordinates and in azimuth, elevation, and roll.

Additional antennas 32 and 36 may be used to allow the three-dimensional tracking receiver 30 to also monitor the relative position of other objects. In particular antenna 32 attached to a patient support 34 or alternatively to the patient his or herself may be used to track the position of the patient. Similarly, antenna 36 attached to a head-mounted display 40 or otherwise to the head of the physician, may be used to track the location of the physician and in particular the direction of the physician's gaze.

The three-dimensional tracking receiver 30 is connected to an image processor 26 so that the location and orientation of the fluoroscopy machine 10, patient 17, and the physician's gaze may be used to modify an x-ray image obtained by the fluoroscopy machine 10 and provided to the physician via the head-mounted display 40 as will be discussed below. Image processor 26 may be associated with a general purpose processor used for control of the fluoroscopy machine 10.

A conventional display 42 is also connected to image processor 26 to receive an image signal as processed by image processor 26 or unprocessed directly from the image intensifier/camera unit 18.

Figure 3:
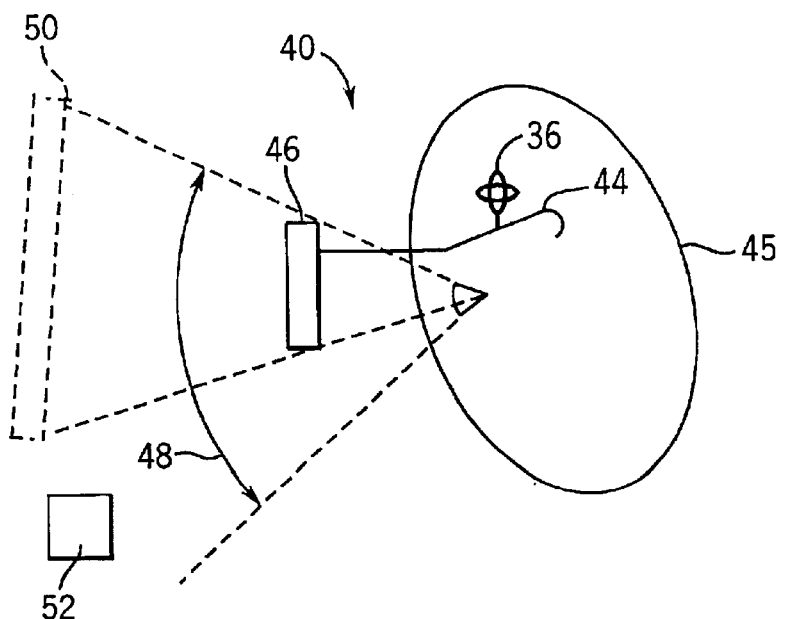
FIG. 3 is a simplified representation of the head-mounted display of FIG. 2 employing opaque display optics positioned at the edge of the physician's field of view.

Referring now to FIG. 3, the head-mounted display 40 provides display optics 46 positioned in fixed relationship to the physician's field of view 48 as held by glasses-like frame 44. The display optics are constructed such that a virtual image 50 is formed having an apparent location in space several feet in front of the physician. Binocular or monocular head mounted displays may be used with the present invention.

In a first version, display optics 46 subtend only a portion of the field of view 48 displaced from the center of the field of view 48. Thus, the physician may view a real object 52 near the center of his or her field of view, then by shifting his or her eyes to the edge of the field of view 48, view the virtual image 50. The display optics 46 may in this case be opaque, that is blocking of light from beyond the display optics 46 within that portion of the field of view subtended.

Figure 4:
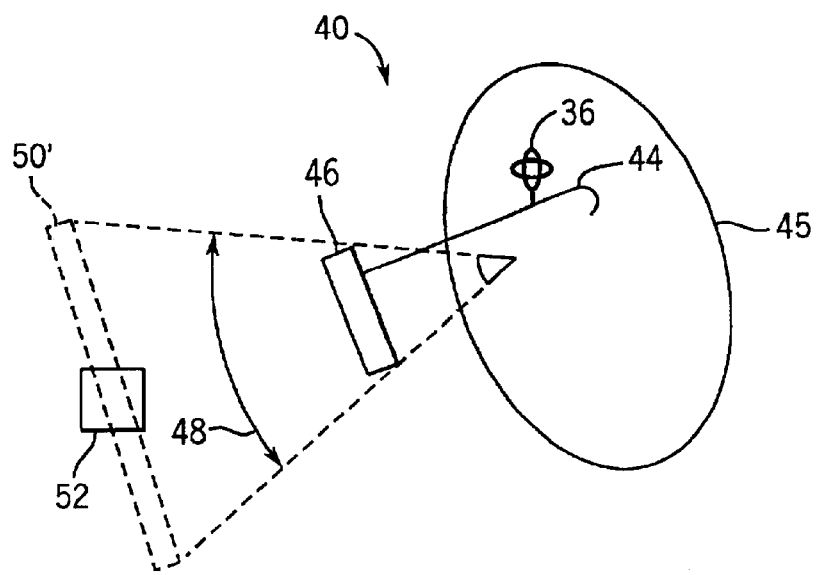
FIG. 4 is a figure similar to that of FIG. 3 showing an alternative head-mounted display employing transparent display optics centered within the physician's field of view.

Referring to FIG. 4 in a second embodiment, the display optics 46 subtend a substantial portion, if not all, of the field of view 48 but are transparent so as to allow light from real object 52 to pass through the display optics 46 so that the virtual image 50' appears semi-transparent and superimposed on real object 52. In both cases, the antenna 36 may be attached to the glasses-like frame 44 so as to provide the indication of the orientation of the gaze of the physician.

Head mounted displays are commercially available from a number of sources including Virtual Research Systems, Inc. of Santa Clara, Calif. under the tradename of i-glasses and Kaiser Electro-Optics Inc. of Carlsbad, Calif. under the tradename of Proview.

Figure 5:
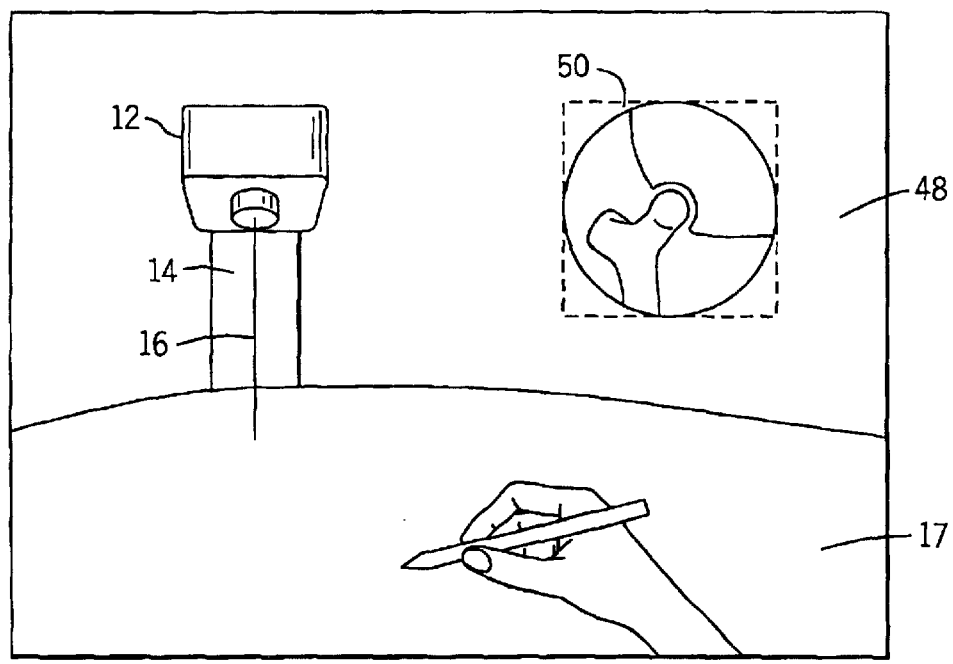
FIG. 5 is a depiction of the physician's field of view when the image provided by the head mounted display is fixed with respect to the physician's field of view.

Referring now to FIG. 5, in a first mode of operation of the present invention, a virtual image 50 is displayed to the physician by the head mounted display 40, displaced to the side of the field of view 48. This image 50 may be essentially the same as that displayed by display 42 and may include no or little image processing. As a result of the physical linking of the display optics 46 (not shown in FIG. 5) to the physician's head, the image 50 floats fixed within the field of view 48 regardless of motion of the physician. By so displacing the virtual image 50 from the center of the field of view 50, the physician's view of the patient 17 is not obstructed and yet the image 50 is always viewable.

In a second embodiment, the image 50 may be processed by the image processor 26 based on input from the three-dimensional tracking receiver 30. In particular, the rotational orientation of the image 50 may be adjusted so that as the physician moves about the patient 17 or as the fluoroscopy machine 10 moves with respect to the patient 17, the image 50 retains rotational linkage with respect to the patient 17 preventing an inversion such as might complicate interventional procedures if the rotated image 50 were relied upon.

Referring now to FIGS. 7 and 8, in such a system, after each frame of video from the image intensifier/camera unit 18 is acquired, as indicated by process block 53, a determination is made as to the relative orientation of the fluoroscopy machine 10 with respect to the physician using antenna 36 and 28 or alternatively, the electrical signals from the collar 20 and gimbal assembly 24 described above. Generally, the physician 45 will have a field of view 56 whose angle 60 that may be determined from antenna 36 as a rotation about an imaginary inferior/superior physician axis 58, the latter normally near vertical. This angle 60 may be compared to a similar angle 61 about axis 16 of the fluoroscopy machine 10 and the difference, corrected for divergence angle α between the physician axis 58 and the x-ray axis 16 according to the sine of α. Thus, if the x-ray axis 16 and physician axis 58 are both vertical, rotation of the physician's head will cause equal rotation of the image 50. In this way, as the physician walks about the patient, for example, the image will rotate so as to present an intuitive orientation to the physician.

The step of computing this rotation is shown in FIG. 7, process block 62, and the display of the given frame is shown by process block 64. This process of blocks 54, 62 and 64 may be repeated as additional frames of x-ray image data are acquired so as to create an essentially real-time correction of the image 50.

Figure 6:
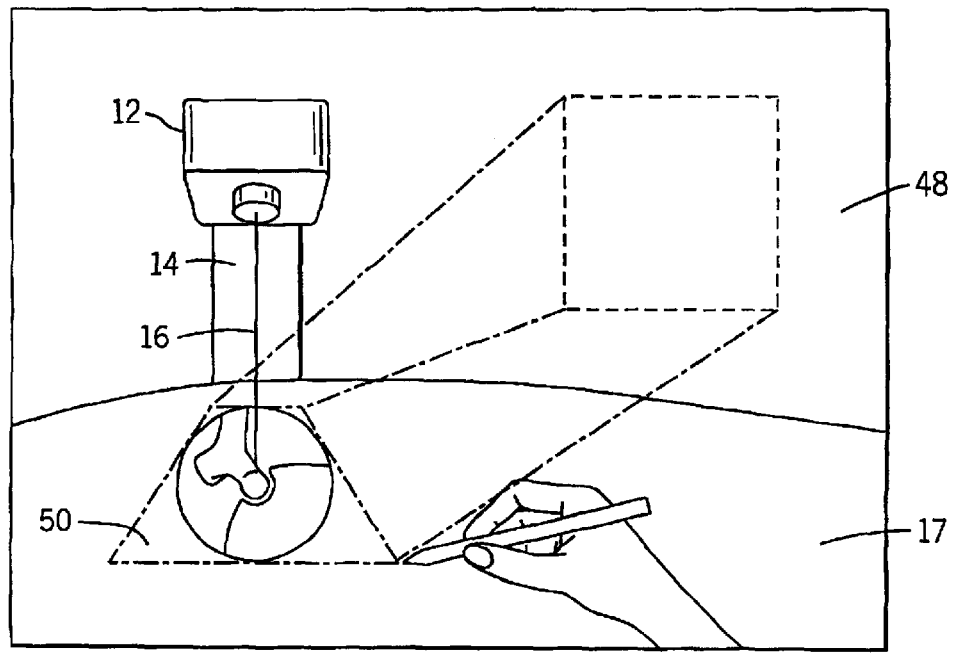
FIG. 6 is a figure similar to that of FIG. 5 where the image provided by the head mounted display is manipulation so as to appear attached to a fixed reference object.

Referring now to FIG. 6, the rotation correction described with respect to FIG. 5, may be augmented by a translation correction and skew correction so as to essentially "attach" the image 50 to an actual object, such as the patient 17. In this way, the location and perspective of the image 50' can closely match that image that would have been obtained with the fluorescent screen of early fluoroscopy machines placed in the same location. For this purpose, a head-mounted display 40 with transparent display optics 46, such as the type described with respect to FIG. 4, is used.

Referring to FIGS. 7 and 9 in the embodiment of FIG. 6, first both the relative angle and the relative location between the physician and the fluoroscopy machine 10 may be obtained at process block 54. A determination of the relative position between the physician and the fluoroscopy machine 10 is obtained simply by subtracting their individual locations with respect to the stationary three-dimensional tracking receiver 30.

Next the location of the image plane 66 must be decided. This may be done by user input by the use of a fourth antenna (not shown) or as a predetermined location with respect to the fluoroscopy machine 10 or the patient 17 using antennas 28 and 32, respectively. For example, an image plane 66 may be established with respect to the fluoroscopy machine 10 independent of the location of the patient 17. Referring to FIG. 1, for example, the image plane 66 may be positioned perpendicular to axis 16 approximately midway between the x-ray source 12 and image intensifier/camera unit 18. In this way, the image plane 66 is intersected by the axis 16 providing a highly intuitive localization of the image plane 66.

After a determination of the relative positions, two manipulations of the image are necessary to affix it to a structure such as the fluoroscopy machine 10. The first is a translation of the image 50 within the field of view 48 and the second is a perspective skewing of the image 50 so as to accommodate the distortion implicit in a possibly oblique image plane 66. Such manipulation of an image to fit a polygon of known orientation is well understood in the art of texture mapping.

The above description has been that of a preferred embodiment of the invention. It will occur to those that practice the art that many modifications may be made without departing from the spirit and scope of the invention. In order to apprise the public of various embodiments that may fall within the scope of the invention the following claims are made.

We claim:

1. A fluoroscopy machine comprising:
   an x-ray source producing a beam of x-rays along an axis;
   a support arm having a first end attached to the x-ray source and having a second end opposite the x-ray source along the axis so as to provide a space along the axis between the first and second ends sufficient to accommodate a human patient;
   an x-ray detector attached to the second end of the arm and positioned to receive the x-rays along the axis and provide image electronic signals;
   a tracking device providing object location and orientation signals an image processor receiving and processing the image electronic signals and the object location and orientation signals to provide adjusted image signals; and
   a display device including:
   (i) image optics producing an image from the adjusted image signals;
   (ii) a head mount for attaching the image optics to a person's head to move therewith and so that the image is displayed to a person wherein the display device is within the person's field of view;

wherein the image is adjusted for at least one of rotation, translation and perspective distortion with respect to the display device.

2. The fluoroscopy machine of claim 1 wherein the image optics are opaque blocking the receipt of light by the person from the person's field of view in the area of the image.

3. The fluoroscopy machine of claim 2 wherein the image optics and head mount displace the image to the edge of the person's field of view.

4. The fluoroscopy machine of claim 1 wherein the image optics are transparent so as to permit the passage of light from the person's field of view through the area of the image.

5. The fluoroscopy machine of claim 1 wherein the object location and orientation signals represent an angle of rotation input processed by the image processor so that the image is rotated to the angle of rotation.

6. The fluoroscopy machine of claim 5 wherein the input is the relative angular displacement between the person's field of view and a reference fixed with respect to the x-ray detector.

7. The fluoroscopy machine of claim 5 wherein the input is the relative angular displacement between the patient and a reference fixed with respect to an imaged patient.

8. The fluoroscopy machine of claim 1 wherein the object location and orientation signals represent a translation input processed by the image processor so that the image is translated within the field of view of the person.

9. The fluoroscopy machine of claim 8 wherein the input is the relative displacement between the person's field of view and a reference fixed with respect to the x-ray detector.

10. The fluoroscopy machine of claim 8 wherein the input is the relative displacement between the patient and a reference fixed with respect to an imaged patient.

11. The fluoroscopy machine of claim 1 wherein the object location and orientation signals represent an image skewing input.

12. The fluoroscopy machine of claim 11 wherein the input is the a relative displacement and orientation between the person's field of view and an image plane fixed with respect to the x-ray detector.

13. The fluoroscopy machine of claim 12 wherein the image plane is intersected by the axis.

14. The fluoroscopy machine of claim 11 wherein the input is the relative displacement and orientation between the person's field of view and an image plane fixed with respect to the patient.

15. The fluoroscopy machine of claim 14 wherein the image plane is intersected by the axis.

* * * * *